(12) United States Patent
Zierenberg

(10) Patent No.: US 8,022,082 B2
(45) Date of Patent: Sep. 20, 2011

(54) METHOD FOR THE ADMINISTRATION OF AN ANTICHOLINERGIC BY INHALATION

(75) Inventor: Bernd Zierenberg, Bingen am Rhein (DE)

(73) Assignee: Boehringer Ingelheim Pharma GmbH & Co., KG, Ingelheim am Rhein (DE)

( * ) Notice: Subject to any disclaimer, the term of this patent is extended or adjusted under 35 U.S.C. 154(b) by 1021 days.

(21) Appl. No.: 11/427,173

(22) Filed: Jun. 28, 2006

(65) Prior Publication Data

US 2006/0251586 A1     Nov. 9, 2006

Related U.S. Application Data

(63) Continuation of application No. 10/407,019, filed on Apr. 4, 2003, now abandoned.

(60) Provisional application No. 60/386,794, filed on Jun. 7, 2002.

(30) Foreign Application Priority Data

Apr. 9, 2002   (EP) .................................. 02007868

(51) Int. Cl.
*A61K 31/46*     (2006.01)
*A61K 9/00*      (2006.01)
*A61K 9/14*      (2006.01)
*A61M 15/00*     (2006.01)

(52) U.S. Cl. ..... 514/291; 424/46; 424/489; 128/203.12; 128/203.15

(58) Field of Classification Search ............ 424/46, 424/489; 514/291; 128/203.12, 203.15
See application file for complete search history.

(56) References Cited

U.S. PATENT DOCUMENTS

| | | |
|---|---|---|
| 4,042,700 A | 8/1977 | Banholzer et al. |
| 4,524,769 A | 6/1985 | Wetterlin et al. |
| 4,608,377 A | 8/1986 | Banholzer et al. |
| 4,627,432 A | 12/1986 | Newell et al. |
| 4,783,534 A | 11/1988 | Banholzer et al. |
| 5,301,666 A | 4/1994 | Lerk et al. |
| 5,544,647 A | 8/1996 | Jewett et al. |
| 5,590,645 A | 1/1997 | Davies et al. |
| 5,610,163 A | 3/1997 | Banholzer et al. |
| 5,647,349 A | 7/1997 | Ohki et al. |
| 5,654,314 A | 8/1997 | Banholzer et al. |
| 5,770,738 A | 6/1998 | Banholzer et al. |
| 5,785,049 A | 7/1998 | Smith et al. |
| 5,826,633 A | 10/1998 | Parks et al. |
| 5,947,118 A | 9/1999 | Hochrainer et al. |
| 5,952,505 A | 9/1999 | Banholzer et al. |
| 6,182,655 B1 | 2/2001 | Keller et al. |
| 6,270,869 B1 | 8/2001 | Zeiter et al. |
| 6,486,321 B2 | 11/2002 | Banholzer et al. |
| 6,506,900 B1 | 1/2003 | Banholzer et al. |
| 6,536,427 B2 | 3/2003 | Davies et al. |
| 6,537,524 B1 * | 3/2003 | Hassan et al. ............ 424/45 |
| 6,608,054 B2 | 8/2003 | Meade et al. |
| 6,620,438 B2 | 9/2003 | Pairet et al. |
| 6,645,466 B1 | 11/2003 | Keller et al. |
| 6,696,042 B2 | 2/2004 | Pairet et al. |
| 6,881,398 B2 | 4/2005 | Myrman et al. |
| 6,884,794 B2 | 4/2005 | Staniforth et al. |
| 6,890,517 B2 | 5/2005 | Drechsel et al. |
| 6,908,928 B2 * | 6/2005 | Banholzer et al. ........... 514/291 |
| 7,070,800 B2 * | 7/2006 | Bechtold-Peters et al. ... 424/434 |
| 7,776,315 B2 | 8/2010 | Pairet et al. |
| 7,854,225 B2 | 12/2010 | Pasbrig et al. |
| 2002/0053344 A1 | 5/2002 | Davies et al. |
| 2002/0110529 A1 | 8/2002 | Bechtold-Peters et al. |
| 2002/0122773 A1 | 9/2002 | Pairet et al. |
| 2002/0137764 A1 | 9/2002 | Drechsel et al. |
| 2002/0151541 A1 | 10/2002 | Pairet et al. |
| 2002/0169181 A1 | 11/2002 | Pairet et al. |
| 2002/0183292 A1 | 12/2002 | Pairet et al. |
| 2002/0183347 A1 | 12/2002 | Meade et al. |
| 2002/0193393 A1 | 12/2002 | Pairet et al. |
| 2003/0070679 A1 | 4/2003 | Hochrainer et al. |
| 2003/0158196 A1 | 8/2003 | Jung et al. |
| 2003/0180227 A1 | 9/2003 | Staniforth et al. |
| 2003/0181478 A1 | 9/2003 | Drechsel et al. |
| 2003/0192540 A1 | 10/2003 | Myrman et al. |

(Continued)

FOREIGN PATENT DOCUMENTS

EP         0 211 595 A2      2/1987

(Continued)

OTHER PUBLICATIONS

Barnes et al. "Tiotropium Bromide (Ba 679 BR), A Novel Long-Acting Muscarinic Antagonist for the Treatment of Obstructive Airways Disease," Life Sciences, 1995, vol. 56, No.s. 11/12, pp. 853-859.*

(Continued)

*Primary Examiner* — James H. Alstrum-Acevedo
(74) *Attorney, Agent, or Firm* — Michael P. Morris; Wendy A. Petka

(57) ABSTRACT

An inhalation kit comprising: (a) an inhaler displaying a flow resistance of about 0.01 to 0.1 $\sqrt{kPa}$ min/L; and (b) an inhalable powder comprising tiotropium in admixture with a physiologically acceptable excipient with an average particle size of between 10 to 500 μm, and a method of administering an inhalable powder containing tiotropium in admixture with a physiologically acceptable excipient with an average particle size of between 10 μm to 500 μm, the method comprising actuating an inhaler a flow resistance of about 0.01 to 0.1 $\sqrt{kPa}$ min/L containing the inhalable powder.

14 Claims, 1 Drawing Sheet

U.S. PATENT DOCUMENTS

Figure 1:
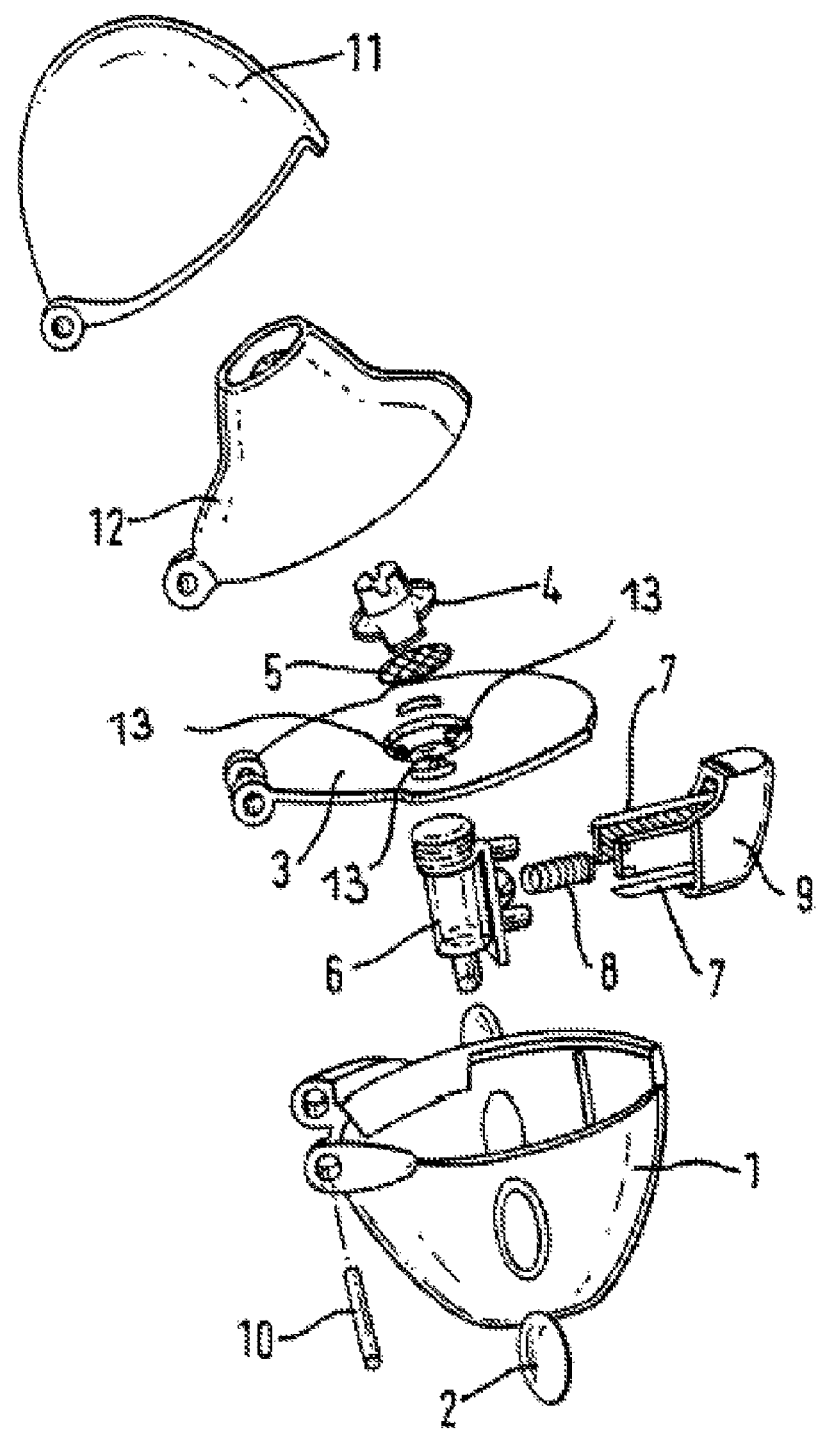

| | | | |
|---|---|---|---|
| 2003/0203925 A1 | 10/2003 | Meade et al. | |
| 2003/0212075 A1 | 11/2003 | Pairet et al. | |
| 2004/0024007 A1 | 2/2004 | Pairet et al. | |
| 2004/0151770 A1 | 8/2004 | Pairet et al. | |
| 2004/0161386 A1 | 8/2004 | Pairet et al. | |
| 2004/0176338 A1 | 9/2004 | Pairet et al. | |
| 2004/0192675 A1 | 9/2004 | Pairet et al. | |
| 2004/0266869 A1 | 12/2004 | Montague et al. | |
| 2005/0055014 A1 | 3/2005 | Coppeta et al. | |
| 2005/0147564 A1 | 7/2005 | Drechsel et al. | |
| 2005/0148562 A1 | 7/2005 | Pairet et al. | |
| 2006/0102511 A1 | 5/2006 | Pasbrig et al. | |
| 2007/0208060 A1* | 9/2007 | Disse | 514/333 |
| 2010/0310477 A1 | 12/2010 | Pairet et al. | |

FOREIGN PATENT DOCUMENTS

| | | |
|---|---|---|
| EP | 0 237 507 A1 | 9/1987 |
| EP | 1 158 970 A | 12/2001 |
| ES | 2 135 690 T3 | 11/1999 |
| GB | 2 169 265 A | 7/1986 |
| JP | 8-059576 A | 3/1996 |
| JP | 8-322933 A | 12/1996 |
| JP | 9-140794 A | 6/1997 |
| JP | 9-140796 A | 6/1997 |
| JP | 9-206378 A | 8/1997 |
| JP | 9-206379 A | 8/1997 |
| JP | 9-206380 A | 8/1997 |
| JP | 9-206381 A | 8/1997 |
| JP | 11-299891 A | 11/1999 |
| WO | 94/04210 A1 | 3/1994 |
| WO | WO 00/28979 | 5/2000 |
| WO | WO 00/47200 | 8/2000 |
| WO | 02/24266 A1 | 3/2002 |
| WO | 02/24268 A1 | 3/2002 |
| WO | 02/36163 A2 | 5/2002 |
| WO | 02/36591 A2 | 5/2002 |
| WO | 02/069945 A2 | 9/2002 |
| WO | 03/084502 A1 | 10/2003 |

OTHER PUBLICATIONS

Allen, D, "High-Barrier Materials for Blister Packaging, *Pharmaceutical & Medical Packaging News*, Originally Published Sep. 2000," downloaded on Mar. 10, 2006 from www/devicelink.com/pmpn/archive/00/09/005.html.

Barry, C, "New plastics transform blister packs into barrier bonanzas: As pharmaceutical manufacturers adopt blister packaging at breathtaking rates, newer, more efficient plastic materials are able to keep up with performance demands—Blister packaging, *Food and Drug Packaging*, Aug. 2002," downloaded Mar. 10, 2006, from findarticles.com/p/articles/mi_m0UQX/is_8_66/ai_91155876.

"College Ter Beoordeling van Geneesmiddelen Medicines Evaluation Board, Public Assessment Report, RVG 26191, Spiriva® 18 mg inhalation powder in hard capsules," ("PAR") was issued by the Medicines Evaluation Board of the Netherlands on May 21, 2002.

Glimm Stefan; "Aluminum Foil—A versatile Tool for Pharmaceutical Packaging", Summer, 2002.

Köhler, Dieter et al; Theory and Practice of Inhalation Therapy; Published by Arcis pp. 1-16, Munich, 2000.

Martineau, William; "Future Pharmaceutical Packaging Trends in the US—An Insight", Autumn, 2002.

Ross, Danna L. et al; Effect of Inhalation Flow Rate on the Dosing Characteristics of Dry Powder Inhaler (DPI) and Metered Dose Inhaler (MDI) Products; Journal of Aerosol Medicine; vol. 9, No. 2, 1996 p. 215 to 226.

* cited by examiner

METHOD FOR THE ADMINISTRATION OF AN ANTICHOLINERGIC BY INHALATION

RELATED APPLICATIONS

This application is a continuation of U.S. application Ser. No. 10/407,019, filed Apr. 4, 2003, which claims benefit of U.S. provisional application No. 60/386,794, filed Jun. 7, 2002, the contents of which are herein incorporated by reference.

FIELD OF THE INVENTION

The invention relates to a method for the administration of powdered preparations containing tiotropium by inhalation.

BACKGROUND OF THE INVENTION

Tiotropium bromide is known from European Patent Application EP 418 716 A1 and has the following chemical structure:

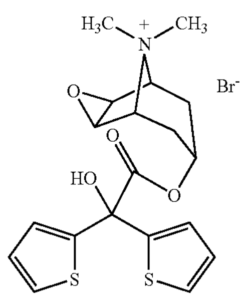

Tiotropium bromide is a highly effective anticholinergic with a long-lasting activity which can be used to treat respiratory complaints, particularly chronic obstructive pulmonary disease (COPD) and asthma. The term tiotropium refers to the free ammonium cation.

For treating the abovementioned complaints, it is useful to administer the active substance by inhalation. In addition to the administration of broncholytically active compounds in the form of metered aerosols and inhalable solutions, the use of inhalable powders containing active substance is of particular importance.

With active substances which have a particularly high efficacy, only small amounts of the active substance are needed per single dose to achieve the desired therapeutic effect. In such cases, the active substance has to be diluted with suitable excipients in order to prepare the inhalable powder. Because of the large amount of excipient, the properties of the inhalable powder are critically influenced by the choice of excipient. When choosing the excipient, its particle size is particularly important. As a rule, the finer the excipient, the poorer its flow properties. However, good flow properties are a prerequisite for highly accurate metering when packing and dividing up the individual doses of preparation, e.g., when producing capsules for powder inhalation or when the patient is metering the individual dose before using a multi-dose inhaler. It has also been found that the particle size of the excipient has a considerable influence on the proportion of active substance in the inhalable powder which is delivered for inhalation. The term inhalable proportion of active substance refers to the particles of the inhalable powder which are conveyed deep into the branches of the lungs when inhaled with a breath. The particle size required for this is between 1 μm and 10 μm, preferably less than 5 μm.

Finally, it has been found that the intended therapeutic effect upon the administration of a pharmaceutical composition via inhalation can be decisively influenced by the inhalation device.

Accordingly, the aim of the invention is to provide for a therapeutically efficient method for the administration of inhalable powders containing tiotropium. Another object of the invention is to provide for an inhalation kit comprising a tiotropium containing powder and an inhalation device, the kit being applicable in the method for administration mentioned before.

BRIEF DESCRIPTION OF THE DRAWINGS

FIG. 1: Exploded view of a preferred inhaler for administration of the pharmaceutical compositions described herein

DETAILED DESCRIPTION OF THE INVENTION

In the method according to the invention an inhalable powder containing tiotropium, preferably in an amount of 0.001% to 5%, in admixture with a physiologically acceptable excipient is administered.

Of particular interest for the method according to the invention is an inhalable powder containing 0.01% to 2%, preferably 0.04% to 0.8%, more preferably 0.08% to 0.64% tiotropium in admixture with a physiologically acceptable excipient is administered.

More preferably in the method according to the invention an inhalable powder containing 0.1% to 0.4% tiotropium in admixture with a physiologically acceptable excipient is administered.

By tiotropium is meant the free ammonium cation. The counter-ion (anion) may be chloride, bromide, iodide, methanesulfonate, p-toluenesulfonate, or methylsulfate. Of these anions, the bromide is preferred.

Accordingly, the method according to the present invention preferably relates to inhalable powders which contain tiotropium in form of tiotropium bromide in an amount of 0.0012% to 6.02%, in admixture with a physiologically acceptable excipient. Of particular interest for the method according to the invention is an inhalable powder containing 0.012% to 2.41%, preferably 0.048% to 0.96%, more preferably 0.096% to 0.77%, tiotropium bromide in admixture with a physiologically acceptable excipient is administered.

More preferably in the method according to the invention an inhalable powder containing 0.12% to 0.48% tiotropium bromide in admixture with a physiologically acceptable excipient is administered.

Tiotropium bromide is, depending on the choice of reaction conditions and solvents, obtainable in different crystalline modifications. Most preferred according to the invention are those powder preparations, that contain tiotropium in form of the crystalline tiotropium bromide monohydrate. Accordingly, the powdered preparations obtainable according to the invention preferably contain 0.0012% to 6.25% crystalline tiotropium bromide monohydrate in admixture with a physiologically acceptable excipient is administered. Of particular interest for the method according to the invention is an inhalable powder containing 0.0125% to 2.5%, preferably 0.05% to 1%, more preferably 0.1% to 0.8%, crystalline tiotropium bromide monohydrate in admixture with a physiologically acceptable excipient is administered.

More preferably in the method according to the invention an inhalable powder containing 0.12% to 0.5% crystalline tiotropium bromide monohydrate in admixture with a physiologically acceptable excipient is administered.

Examples of physiologically acceptable excipients which may be used to prepare the inhalable powders applicable according to the invention include, for example, monosaccharides (e.g., glucose or arabinose), disaccharides (e.g., lactose, saccharose, or maltose), oligo- and polysaccharides (e.g., dextrane), polyalcohols (e.g., sorbitol, mannitol, or xylitol), salts (e.g., sodium chloride or calcium carbonate) or mixtures of these excipients with one another. Preferably, mono- or disaccharides are used, while the use of lactose or glucose is preferred, particularly, but not exclusively, in the form of their hydrates, preferably in the form of their monohydrates.

In the method according to the invention, the average particle size of the physiologically acceptable excipient is preferably between 10 μm to 500 μm, more preferably between 15 μm to 200 μm, most preferably between 20 μm to 100 μm. If not otherwise emphasized, the term average particle size according to the invention is to be understood as the Mass Median Aerodynamic Diameter (MMAD). Methods for the determination thereof are known in the art.

Besides the coarser particle fraction of the excipient mentioned hereinbefore, the excipient can optionally additionally contain a specifically added fraction of excipient of finer particle size. This finer particle size fraction is characterized by an average particle size of 1 μm to 9 μm, preferably 2 μm to 8 μm, more preferably 3 μm to 7 μm.

If a finer particle fraction is present, the proportion of finer excipient in the total amount of excipient is 1% to 20%, preferably 3% to 15%, more preferably 5% to 10%. When reference is made to a mixture within the scope of the present invention, this always means a mixture obtained by mixing together clearly defined components. Accordingly, when an excipient mixture of coarser and finer excipients is mentioned, this can only denote mixtures obtained by mixing a coarser excipient component with a finer excipient component.

The percentages given within the scope of the present invention are always percent by weight.

In the method according to the invention, the inhalable powders mentioned hereinbefore may efficiently be administered using inhalers that are characterized by a specific flow resistance (R).

The flow resistance of inhalers can be calculated via the following formula:

$$v = \frac{1}{R} \cdot \sqrt{p}$$

wherein:
v is the volumetric flow rate (L/min);
p is the pressure drop (kPa); and
R is the flow resistance.

In the method according to the invention, the flow resistance R characterizing the inhaler is in a range of about 0.01 to 0.1 $\sqrt{kPa}$ min/L preferably in the range of about 0.02 to 0.06 $\sqrt{kPa}$ min/L.

Accordingly, the invention relates to a method for the administration of an inhalable powder containing tiotropium, preferably in an amount of 0.001% to 5%, in admixture with a physiologically acceptable excipient with an average particle size of between 10 μm to 500 μm, and further characterized in that the tiotropium containing powder is administered by an inhaler displaying a flow resistance of about 0.01 to 0.1 $\sqrt{kPa}$ min/L.

In another embodiment, the invention relates to a method for the treatment of airway diseases, particularly chronic obstructive pulmonary disease (COPD) and asthma, characterized in that an inhalable powder containing tiotropium, preferably in an amount of 0.001% to 5%, in admixture with a physiologically acceptable excipient with an average particle size of between 10 μm to 500 μm, is administered via inhalation by an inhaler displaying a flow resistance of about 0.01 to 0.1 $\sqrt{kPa}$ min/L.

In another embodiment, the invention relates to the use of an inhaler for the administration of a tiotropium containing inhalable powder via inhalation, characterized in that the inhalable powder contains tiotropium, preferably in an amount of 0.001% to 5%, in admixture with a physiologically acceptable excipient with an average particle size of between 10 μm to 500 μm, and further characterized in that the inhaler displays a flow resistance of about 0.01 to 0.1 $\sqrt{kPa}$ min/L.

In yet another embodiment the invention relates to an inhalation kit consisting of an inhaler displaying a flow resistance of about 0.01 to 0.1 $\sqrt{kPa}$ min/L and an inhalable powder containing tiotropium, preferably in an amount of 0.001% to 5%, in admixture with a physiologically acceptable excipient with an average particle size of between 10 μm to 500 μm.

In another preferred embodiment according to the invention, the inhaler described in FIG. 1 is applied. For the administration of tiotropium containing powders by inhalation by means of the inhaler according to FIG. 1, it is required to fill appropriate amounts of the powder into capsules. Methods for filling powders into capsules are known in the art.

The inhaler according to FIG. 1 is characterized by a housing 1 containing two windows 2, a deck 3 in which there are air inlet ports and which is provided with a screen 5 secured via a screen housing 4, an inhalation chamber 6 connected to the deck 3 on which there is a push button 9 provided with two sharpened pins 7 and movable counter to a spring 8, a mouthpiece 12 which is connected to the housing 1, the deck 3 and a cover 11 via a spindle 10 to enable it to be flipped open or shut and three holes 13 with diameters below 1 mm in the central region around the capsule chamber 6 and underneath the screen housing 4 and screen 5.

The main air flow enters the inhaler between deck 3 and base 1 near to the hinge. The deck has in this range a reduced width, which forms the entrance slit for the air. Then the flow reverses and enters the capsule chamber 6 through the inlet tube. The flow is then further conducted through the filter and filter holder to the mouthpiece. A small portion of the flow enters the device between mouthpiece and deck and flows then between filter holder and deck into the main stream. Due to production tolerances, there is some uncertainty in this flow because of the actual width of the slit between filter holder and deck. In case of new or reworked tools, the flow resistance of the inhaler may therefore be a little off the target value. To correct this deviation, the deck has in the central region around the capsule chamber 6 and underneath the screen housing 4 and screen 5 three holes 13 with diameters below 1 mm. Through these holes 13 flows air from the base into the main air stream and reduces such slightly the flow resistance of the inhaler. The actual diameter of these holes 13 can be chosen by proper inserts in the tools so that the mean flow resistance can be made equal to the target value.

Accordingly, in a preferred embodiment the invention relates to a method for the administration of an inhalable powder containing tiotropium, preferably in an amount of 0.001% to 5%, in admixture with a physiologically acceptable excipient with an average particle size of between 10 μm to 500 μm, by means of the inhaler according to FIG. 1, comprising a housing, containing two windows, a deck in which there are air inlet ports and which is provided with a screen secured via a screen housing, an inhalation chamber connected to the deck on which there is a push button provided with two sharpened pins and movable counter to a spring, a mouthpiece which is connected to the housing, the deck and a cover via a spindle to enable it to be flipped open or shut, and three holes with diameters below 1 mm in the central region around the capsule chamber and underneath the screen housing and screen.

In another embodiment, the invention relates to a method for treatment of airway diseases, particularly chronic obstructive pulmonary disease and asthma, characterized in that an inhalable powder containing tiotropium, preferably in an amount of 0.001% to 5%, in admixture with a physiologically acceptable excipient with an average particle size of between 10 µm to 500 µm, is administered via inhalation by the inhaler according to FIG. 1, comprising a housing, containing two windows, a deck in which there are air inlet ports and which is provided with a screen secured via a screen housing, an inhalation chamber connected to the deck on which there is a push button provided with two sharpened pins and movable counter to a spring, a mouthpiece which is connected to the housing, the deck and a cover via a spindle to enable it to be flipped open or shut, and three holes with diameters below 1 mm in the central region around the capsule chamber and underneath the screen housing and screen.

In another preferred embodiment, the invention relates to the use of the inhaler according to FIG. 1, comprising a housing, containing two windows, a deck in which there are air inlet ports and which is provided with a screen secured via a screen housing, an inhalation chamber connected to the deck on which there is a push button provided with two sharpened pins and movable counter to a spring, a mouthpiece which is connected to the housing, the deck and a cover via a spindle to enable it to be flipped open or shut, and three holes with diameters below 1 mm in the central region around the capsule chamber and underneath the screen housing and screen, for the administration of an inhalable powdered containing tiotropium, preferably in an amount of 0.001% to 5%, in admixture with a physiologically acceptable excipient with an average particle size of between 10 µm to 500 µm.

In yet another preferred embodiment, the invention relates to an inhalation kit consisting of an inhalable powdered containing tiotropium, preferably in an amount of 0.001% to 5%, in admixture with a physiologically acceptable excipient with an average particle size of between 10 µm to 500 µm, and the inhaler according to FIG. 1, comprising a housing, containing two windows, a deck in which there are air inlet ports and which is provided with a screen secured via a screen housing, an inhalation chamber connected to the deck on which there is a push button provided with two sharpened pins and movable counter to a spring, a mouthpiece which is connected to the housing, the deck and a cover via a spindle to enable it to be flipped open or shut, and three holes with diameters below 1 mm in the central region around the capsule chamber and underneath the screen housing and screen.

In another preferred embodiment according to the invention the inhaler according to U.S. Pat. No. 4,524,769 is applied. This inhaler (or inhalator) is activated by the air flow generated at inhalation. The disclosure of U.S. Pat. No. 4,524,769 is incorporated herein by reference in its entirety.

Accordingly, in a preferred embodiment, the invention relates to a method for the administration of an inhalable powder containing tiotropium, preferably in an amount of 0.001% to 5%, in admixture with a physiologically acceptable excipient with an average particle size of between 10 µm to 500 µm, by means of the inhaler according to U.S. Pat. No. 4,524,769, comprising a nozzle, a conduit connected to the nozzle, a storage chamber adjacent the conduit for storing the inhalable powder to be dispensed by the inhalator, a perforated membrane having a plurality of preselected perforated portions each holding and dispensing a reproducible unit dose of less than 50 mg of the inhalable powder, the membrane being mounted for movement between the conduit and the storage chamber so that one of the preselected portions is positioned across the conduit whereby the active compound held in the perforation thereof can be dispensed into the conduit and another of the preselected portions thereof is disposed within the storage chamber, dose loading means for introducing the inhalable powder in the storage chamber into the perforation of the preselected portion of the membrane disposed within the storage chamber, and maneuvering means for displacing the perforated membrane through a plurality of positions whereby successive preselected portions of the perforated membrane holding the inhalable powder are positioned across the conduit for dispensing the inhalable powder.

In another embodiment, the invention relates to a method for treatment of airway diseases, particularly chronic obstructive pulmonary disease and asthma, characterized in that an inhalable powder containing tiotropium, preferably in an amount of 0.001% to 5%, in admixture with a physiologically acceptable excipient with an average particle size of between 10 µm to 500 µm, is administered via inhalation by the inhaler according to U.S. Pat. No. 4,524,769, comprising a nozzle, a conduit connected to the nozzle, a storage chamber adjacent the conduit for storing the inhalable powder to be dispensed by the inhalator, a perforated membrane having a plurality of preselected perforated portions each holding and dispensing a reproducible unit dose of less than 50 mg of the inhalable powder, the membrane being mounted for movement between the conduit and the storage chamber so that one of the preselected portions is positioned across the conduit whereby the active compound held in the perforation thereof can be dispensed into the conduit and another of the preselected portions thereof is disposed within the storage chamber, dose loading means for introducing the inhalable powder in the storage chamber into the perforation of the preselected portion of the membrane disposed within the storage chamber, and maneuvering means for displacing the perforated membrane through a plurality of positions whereby successive preselected portions of the perforated membrane holding the inhalable powder are positioned across the conduit for dispensing the inhalable powder.

In another preferred embodiment, the invention relates to the use of the inhaler according to U.S. Pat. No. 4,524,769 comprising a nozzle, a conduit connected to the nozzle, a storage chamber adjacent the conduit for storing the inhalable powder to be dispensed by the inhalator, a perforated membrane having a plurality of preselected perforated portions each holding and dispensing a reproducible unit dose of less than 50 mg of the inhalable powder, the membrane being mounted for movement between the conduit and the storage chamber so that one of the preselected portions is positioned across the conduit whereby the active compound held in the perforation thereof can be dispensed into the conduit and another of the preselected portions thereof is disposed within the storage chamber, dose loading means for introducing the inhalable powder in the storage chamber into the perforation of the preselected portion of the membrane disposed within the storage chamber, and maneuvering means for displacing the perforated membrane through a plurality of positions whereby successive preselected portions of the perforated membrane holding the inhalable powder are positioned across the conduit for dispensing the inhalable powder, for the administration of an inhalable powdered containing tiotropium, preferably in an amount of 0.001% to 5%, in admixture with a physiologically acceptable excipient with an average particle size of between 10 μm to 500 μm.

In yet another preferred embodiment, the invention relates to an inhalation kit consisting of an inhalable powdered containing tiotropium, preferably in an amount of 0.001% to 5%, in admixture with a physiologically acceptable excipient with an average particle size of between 10 μm to 500 μm, and the inhaler according to U.S. Pat. No. 4,524,769, comprising a nozzle, a conduit connected to the nozzle, a storage chamber adjacent the conduit for storing the inhalable powder to be dispensed by the inhalator, a perforated membrane having a plurality of preselected perforated portions each holding and dispensing a reproducible unit dose of less than 50 mg of the inhalable powder, the membrane being mounted for movement between the conduit and the storage chamber so that one of the preselected portions is positioned across the conduit whereby the active compound held in the perforation thereof can be dispensed into the conduit and another of the preselected portions thereof is disposed within the storage chamber, dose loading means for introducing the inhalable powder in the storage chamber into the perforation of the preselected portion of the membrane disposed within the storage chamber, and maneuvering means for displacing the perforated membrane through a plurality of positions whereby successive preselected portions of the perforated membrane holding the inhalable powder are positioned across the conduit for dispensing the inhalable powder.

In another preferred embodiment according to the invention, the inhaler according to U.S. Pat. No. 5,590,645 is applied. The disclosure of U.S. Pat. No. 5,590,645 is incorporated herein by reference in its entirety.

Accordingly, in a preferred embodiment, the invention relates to a method for the administration of an inhalable powder containing tiotropium, preferably in an amount of 0.001% to 5%, in admixture with a physiologically acceptable excipient with an average particle size of between 10 μm to 500 μm, by means of the inhaler according to U.S. Pat. No. 5,590,645, comprising a medicament pack having a plurality of containers for containing medicament in powder form wherein the containers are spaced along the length of and defined between two peelable sheets secured to each other, an opening station for receiving a container of the medicament pack being, means positioned to engage peelable sheets of a container which has been received in the opening station for peeling apart the peelable sheets, to open such a container, an outlet, positioned to be in communication with an opened container, through which a user can inhale medicament in powder form from such an opened container, and indexing means for indexing in communication with the outlet containers of a medicament pack in use with the inhalation device.

In another embodiment, the invention relates to a method for treatment of airway diseases, particularly chronic obstructive pulmonary disease and asthma, characterized in that an inhalable powder containing tiotropium, preferably in an amount of 0.001% to 5%, in admixture with a physiologically acceptable excipient with an average particle size of between 10 μm to 500 μm, is administered via inhalation by the inhaler according to U.S. Pat. No. 5,590,645, comprising a medicament pack having a plurality of containers for containing medicament in powder form wherein the containers are spaced along the length of and defined between two peelable sheets secured to each other, an opening station for receiving a container of the medicament pack being, means positioned to engage peelable sheets of a container which has been received in the opening station for peeling apart the peelable sheets, to open such a container, an outlet, positioned to be in communication with an opened container, through which a user can inhale medicament in powder form from such an opened container, and indexing means for indexing in communication with the outlet containers of a medicament pack in use with the inhalation device.

In another preferred embodiment, the invention relates to the use of the inhaler according to U.S. Pat. No. 5,590,645, comprising a medicament pack having a plurality of containers for containing medicament in powder form wherein the containers are spaced along the length of and defined between two peelable sheets secured to each other, an opening station for receiving a container of the medicament pack being, means positioned to engage peelable sheets of a container which has been received in the opening station for peeling apart the peelable sheets, to open such a container, an outlet, positioned to be in communication with an opened container, through which a user can inhale medicament in powder form from such an opened container, and indexing means for indexing in communication with the outlet containers of a medicament pack in use with the inhalation device, for the administration of an inhalable powdered containing tiotropium, preferably in an amount of 0.001% to 5%, in admixture with a physiologically acceptable excipient with an average particle size of between 10 μm to 500 μm.

In yet another preferred embodiment, the invention relates to an inhalation kit consisting of an inhalable powdered containing tiotropium, preferably in an amount of 0.001% to 5%, in admixture with a physiologically acceptable excipient with an average particle size of between 10 μm to 500 μm, and the inhaler according to U.S. Pat. No. 5,590,645, comprising a medicament pack having a plurality of containers for containing medicament in powder form wherein the containers are spaced along the length of and defined between two peelable sheets secured to each other, an opening station for receiving a container of the medicament pack being, means positioned to engage peelable sheets of a container which has been received in the opening station for peeling apart the peelable sheets, to open such a container, an outlet, positioned to be in communication with an opened container, through which a user can inhale medicament in powder form from such an opened container, and indexing means for indexing in communication with the outlet containers of a medicament pack in use with the inhalation device.

In another preferred embodiment according to the invention, the inhaler according to U.S. Pat. No. 4,627,432 is applied. The disclosure of U.S. Pat. No. 4,627,432 is incorporated herein by reference in its entirety.

Accordingly, in a preferred embodiment, the invention relates to a method for the administration of an inhalable powder containing tiotropium, preferably in an amount of 0.001% to 5%, in admixture with a physiologically acceptable excipient with an average particle size of between 10 μm to 500 μm, by means of the inhaler according to U.S. Pat. No. 4,627,432, being characterized by a housing with a chamber therein, an air inlet into the chamber, a circular disc having an axis substantially coaxial to the chamber axis and rotatable inside the chamber and provided with a plurality of apertures therethrough arranged in a circle, the apertures being sized and positioned so that each aperture is adapted to be aligned with a different container, the disc being arranged so that the carrier can be placed in contact with one face of the disc with one of the containers located in each one of the apertures, an outlet through which a patient may inhale leading out of the chamber, an opening in the housing alignable with respective ones of the apertures in the disc as the disc is rotated, a plunger operatively connected to the housing and having a penetrating member, the penetrating member being displaceable to pass through the opening and the corresponding aperture in the disc registered with it thereby to penetrate and open a container located in the aperture so that the medicament will be released from the container and entrained in the air flow produced by a patient inhaling through the outlet, and means between the disc and the housing for rotatably indexing the disc to register each of the apertures in turn with the housing opening.

In another embodiment, the invention relates to a method for treatment of airway diseases, particularly chronic obstructive pulmonary disease and asthma, characterized in that an inhalable powder containing tiotropium, preferably in an amount of 0.001% to 5%, in admixture with a physiologically acceptable excipient with an average particle size of between 10 μm to 500 μm, is administered via inhalation by the inhaler according to U.S. Pat. No. 4,627,432, being characterized by a housing with a chamber therein, an air inlet into the chamber, a circular disc having an axis substantially coaxial to the chamber axis and rotatable inside the chamber and provided with a plurality of apertures therethrough arranged in a circle, the apertures being sized and positioned so that each aperture is adapted to be aligned with a different container, the disc being arranged so that the carrier can be placed in contact with one face of the disc with one of the containers located in each one of the apertures, an outlet through which a patient may inhale leading out of the chamber, an opening in the housing alignable with respective ones of the apertures in the disc as the disc is rotated, a plunger operatively connected to the housing and having a penetrating member, the penetrating member being displaceable to pass through the opening and the corresponding aperture in the disc registered with it thereby to penetrate and open a container located in the aperture so that the medicament will be released from the container and entrained in the air flow produced by a patient inhaling through the outlet, and means between the disc and the housing for rotatably indexing the disc to register each of the apertures in turn with the housing opening.

In another preferred embodiment, the invention relates to the use of the inhaler according to U.S. Pat. No. 4,627,432 being characterized by a housing with a chamber therein, an air inlet into the chamber, a circular disc having an axis substantially coaxial to the chamber axis and rotatable inside the chamber and provided with a plurality of apertures therethrough arranged in a circle, the apertures being sized and positioned so that each aperture is adapted to be aligned with a different container, the disc being arranged so that the carrier can be placed in contact with one face of the disc with one of the containers located in each one of the apertures, an outlet through which a patient may inhale leading out of the chamber, an opening in the housing alignable with respective ones of the apertures in the disc as the disc is rotated, a plunger operatively connected to the housing and having a penetrating member, the penetrating member being displaceable to pass through the opening and the corresponding aperture in the disc registered with it thereby to penetrate and open a container located in the aperture so that the medicament will be released from the container and entrained in the air flow produced by a patient inhaling through the outlet, and means between the disc and the housing for rotatably indexing the disc to register each of the apertures in turn with the housing opening, for the administration of an inhalable powdered containing tiotropium, preferably in an amount of 0.001% to 5%, in admixture with a physiologically acceptable excipient with an average particle size of between 10 μm to 500 μm.

In yet another preferred embodiment, the invention relates to an inhalation kit consisting of an inhalable powdered containing tiotropium, preferably in an amount of 0.001 to 5%, in admixture with a physiologically acceptable excipient with an average particle size of between 10 to 500 μm, and the inhaler according to U.S. Pat. No. 4,627,432, being characterized by a housing with a chamber therein, an air inlet into the chamber, a circular disc having an axis substantially coaxial to the chamber axis and rotatable inside the chamber and provided with a plurality of apertures therethrough arranged in a circle, the apertures being sized and positioned so that each aperture is adapted to be aligned with a different container, the disc being arranged so that the carrier can be placed in contact with one face of the disc with one of the containers located in each one of the apertures, an outlet through which a patient may inhale leading out of the chamber, an opening in the housing alignable with respective ones of the apertures in the disc as the disc is rotated, a plunger operatively connected to the housing and having a penetrating member, the penetrating member being displaceable to pass through the opening and the corresponding aperture in the disc registered with it thereby to penetrate and open a container located in the aperture so that the medicament will be released from the container and entrained in the air flow produced by a patient inhaling through the outlet, and means between the disc and the housing for rotatably indexing the disc to register each of the apertures in turn with the housing opening.

The following Examples serve to illustrate the present invention further without restricting its scope to the embodiments provided hereinafter by way of example.

Starting Materials

As a starting material for the synthesis of crystalline tiotropium bromide monohydrate tiotropium bromide obtained according to the disclosure of European patent application EP 418 716 A1 is be used.

Preparation of Crystalline Tiotropium Bromide Monohydrate 15.0 kg of tiotropium bromide as obtained according to the methods disclosed in EP 418 716 A1 are added to 25.7 kg of water in a suitable reaction vessel. The mixture is heated to 80° C. to 90° C. and stirred at constant temperature until a clear solution is formed. Activated charcoal (0.8 kg) moistened with water, is suspended in 4.4 kg of water, this mixture is added to the solution containing the tiotropium bromide and rinsed with 4.3 kg of water. The mixture thus obtained is stirred for at least 15 minutes at 80° C. to 90° C. and then filtered through a heated filter into an apparatus which has been preheated to an outer temperature of 70° C. The filter is rinsed with 8.6 kg of water. The contents of the apparatus is cooled at 3° C. to 5° C. every 20 minutes to a temperature of 20° C. to 25° C. The apparatus is further cooled to 10° C. to 15° C. using cold water and crystallization is completed by stirring for at least one hour. The crystals are isolated using a suction drier, the crystal slurry isolated is washed with 9 liters of cold water (10° C. to 15° C.) and cold acetone (10° C. to 15° C.). The crystals obtained are dried in a nitrogen current at 25° C. over 2 hours. Yield: 13.4 kg of tiotropium bromide monohydrate (86% of theory)

The crystalline tiotropium bromide monohydrate thus obtained is micronized by known methods, to bring the active substance into the average particle size which meets the specifications according to the invention.

The DSC diagram of crystalline tiotropium bromide monohydrate shows two characteristic signals. The first, relatively broad, endothermic signal between 50° C. to 120° C. can be attributed to the dehydration of the tiotropium bromide monohydrate to produce the anhydrous form. The second, relatively sharp endothermic peak at 230° C.±5° C. can be put down to the melting of the substance. These data were obtained using a Mettler DSC 821 and evaluated with the Mettler STAR software package. These data, like the other values given in the above Table, were obtained at a heating rate of 10 K/min.

The crystalline tiotropium bromide monohydrate thus obtained was characterized by IR spectroscopy. The data was obtained using a Nicolet FTIR spectrometer and evaluated with the Nicolet OMNIC software package, version 3.1. The measurement was carried out with 2.5 μmol of tiotropium bromide monohydrate in 300 mg of KBr. Table 1 shows some of the essential bands of the IR spectrum.

TABLE 1

Attribution of Specific Bands

| Wave Number (cm$^{-1}$) | Attribution | Type of Oscillation |
|---|---|---|
| 3570, 410 | O—H | elongated oscillation |
| 3105 | Aryl C—H | elongated oscillation |
| 1730 | C=O | elongated oscillation |
| 1260 | Epoxide C—O | elongated oscillation |
| 1035 | Ester C—OC | elongated oscillation |
| 720 | Thiophene | cyclic oscillation |

The crystalline tiotropium bromide monohydrate was characterized by X-ray structural analysis. The measurements of X-ray diffraction intensity were carried out on an AFC7R-4-circuit diffractometer (Rigaku) using monochromatic copper $K_\alpha$ radiation. The structural solution and refinement of the crystal structure were obtained by direct methods (SHELXS86 Program) and FMLQ-refinement (TeXsan Program). The X-ray structural analysis carried out showed that crystalline tiotropium bromide hydrate has a simple monoclinic cell with the following dimensions: a=18.0774 Å, b=11.9711 Å, c=9.9321 Å, β=102.691°, V=2096.96 Å$^3$.

Apparatus

The following machines and equipment, for example, may be used to prepare the inhalable powders according to the invention:

Mixing Container or Powder Mixer: Gyrowheel mixer 200 L; type: DFW80N-4; made by: Messrs Engelsmann, D-67059 Ludwigshafen.

Granulating Sieve: Quadro Comil; type: 197-S; made by: Messrs Joisten & Kettenbaum, D-51429 Bergisch-Gladbach.

The following examples provide for inhalable powder mixtures applicable according to the invention.

Example 1

5.2 kg of glucose monohydrate for inhalation (average particle size 25 μm) is used as the excipient. 22.5 g crystalline tiotropium bromide monohydrate (micronized; average particle size 1 μm to 3.5 μm) is used as the active ingredient.

The aforementioned components are sieved in in alternate layers of lactose monohydrate in batches of about 200 g and crystalline tiotropium bromide monohydrate in batches of about 1 g. The ingredients sieved in are then mixed together (mixing at 900 rpm).

According to the invention, preferably 5.2225 mg of the aforementioned powder is delivered per dose.

Example 2

5.4775 kg of lactose monohydrate for inhalation (average particle size 25 μm) is used as the excipient. 22.5 g crystalline tiotropium bromide monohydrate (micronized; average particle size 1 to 3.5 μm) is used as the active ingredient.

The aforementioned components are sieved in in alternate layers of lactose monohydrate in batches of about 200 g and crystalline tiotropium bromide monohydrate in batches of about 1 g. The ingredients sieved in are then mixed together (mixing at 900 rpm).

According to the invention, preferably 5.5 mg of the aforementioned powder are delivered per dose.

Example 3

1.1: Excipient Mixture 5.203 kg of lactose monohydrate for inhalation (average particle size 25 μm) is used as the coarser excipient component. 0.27 kg of lactose monohydrate (5 μm) is used as the finer excipient component. In the resulting 5,473 kg of excipient mixture, the proportion of the finer excipient component is 5%.

The aforementioned components are sieved in in alternate layers of lactose monohydrate (25 μm) in batches of about 200 g and lactose monohydrate (5 μm) in batches of about 10 g. The ingredients sieved in are then mixed together (mixing at 900 rpm).

1.2: Final Mixture

To prepare the final mixture, 5,473 kg of the excipient mixture (1.1) and 22.5 g crystalline tiotropium bromide monohydrate (micronized; average particle size 1 μm to 3.5 μm) are used. The content of active substance in the resulting powder is 0.4%.

The aforementioned components are sieved in in alternate layers of excipient mixture (1.1) in batches of about 200 g and crystalline tiotropium bromide monohydrate in batches of about 1 g. The ingredients sieved in are then mixed together (mixing at 900 rpm).

According to the invention preferably about 5.5 mg of the aforementioned powder are delivered per dose.

I claim:

1. A method of administering an inhalable powder containing tiotropium in admixture with a physiologically acceptable excipient with an average particle size of between 10 μm to 500 μm, the method comprising actuating an inhaler with a flow resistance of about 0.01 to 0.1 $\sqrt{kPa}$ min/L containing the inhalable powder, wherein the inhaler comprises: a housing containing two windows, a deck in which there are air inlet ports and which is provided with a screen secured by a screen housing, an inhalation chamber connected to the deck on which there is a push button provided with two sharpened pins and movable counter to a spring, a mouthpiece which is connected to the housing, the deck, and a cover via a spindle to enable it to be flipped open or shut, and three holes with diameters below 1 mm in the central region around the capsule chamber and underneath the screen housing and screen.

2. The method according to claim 1, wherein the amount of tiotropium in the inhalable powder is 0.001% to 5% of the inhalable powder.

3. The method according to claim 1, wherein the inhaler has a flow resistance of about 0.02 to 0.06 $\sqrt{kPa}$ min/L.

4. The method according to claim 1, wherein the tiotropium is a chloride, bromide, iodide, methanesulfonate, p-toluenesulfonate, or methylsulfate salt.

5. The method according to claim 4, wherein the tiotropium is crystalline tiotropium bromide monohydrate.

6. An inhalation kit comprising:
   (a) an inhaler displaying a flow resistance of about 0.01 to 0.1 $\sqrt{kPa}$ min/L; and (b) an inhalable powder comprising tiotropium in admixture with a physiologically acceptable excipient with an average particle size of between 10 to 500 µm, wherein the inhaler comprises: a housing containing two windows, a deck in which there are air inlet ports and which is provided with a screen secured by a screen housing, an inhalation chamber connected to the deck on which there is a push button provided with two sharpened pins and movable counter to a spring, a mouthpiece which is connected to the housing, the deck, and a cover via a spindle to enable it to be flipped open or shut, and three holes with diameters below 1 mm in the central region around the capsule chamber and underneath the screen housing and screen.

7. The inhalation kit according to claim 6, wherein the amount of tiotropium in the inhalable powder is 0.001% to 5% of the inhalable powder.

8. The inhalation kit according to claim 7, wherein the tiotropium is a chloride, bromide, iodide, methanesulfonate, p-toluenesulfonate, or methylsulfate salt.

9. The inhalation kit according to claim 8, wherein the tiotropium is crystalline tiotropium bromide monohydrate.

10. The inhalation kit according to claim 6, wherein the flow resistance of the inhaler is about 0.02 to 0.06 $\sqrt{kPa}$ min/L.

11. The inhalation kit according to claim 10, wherein the tiotropium is a chloride, bromide, iodide, methanesulfonate, p-toluenesulfonate, or methylsulfate salt.

12. The inhalation kit according to claim 11, wherein the tiotropium is crystalline tiotropium bromide monohydrate.

13. The inhalation kit according to claim 6, wherein the tiotropium is a chloride, bromide, iodide, methanesulfonate, p-toluenesulfonate, or methylsulfate salt.

14. The inhalation kit according to claim 13, wherein the tiotropium is crystalline tiotropium bromide monohydrate.

* * * * *